United States Patent
Buchanan, III et al.

(10) Patent No.: US 9,239,405 B2
(45) Date of Patent: Jan. 19, 2016

(54) APPARATUS FOR DETECTING PARTICLES

(71) Applicant: Azbil Corporation, Tokyo (JP)

(72) Inventors: John H. Buchanan, III, Tucson, AZ (US); Hisaya Murakami, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 383 days.

(21) Appl. No.: 13/834,062

(22) Filed: Mar. 15, 2013

(65) Prior Publication Data

US 2013/0248693 A1    Sep. 26, 2013

Related U.S. Application Data

(60) Provisional application No. 61/614,395, filed on Mar. 22, 2012.

(51) Int. Cl.
| | |
|---|---|
| *G01N 15/14* | (2006.01) |
| *G01V 8/10* | (2006.01) |
| *G01N 21/64* | (2006.01) |
| *G01N 15/02* | (2006.01) |
| *G01N 15/00* | (2006.01) |
| *G01N 21/53* | (2006.01) |

(52) U.S. Cl.
CPC .............. *G01V 8/10* (2013.01); *G01N 15/0211* (2013.01); *G01N 15/1404* (2013.01); *G01N 15/1459* (2013.01); *G01N 21/6486* (2013.01); *G01N 21/53* (2013.01); *G01N 2015/0046* (2013.01); *G01N 2015/1493* (2013.01); *G01N 2021/6493* (2013.01)

(58) Field of Classification Search
CPC .......................... G01V 8/10; G01N 2015/0693
See application file for complete search history.

(56) References Cited

U.S. PATENT DOCUMENTS

2007/0229825 A1 *  10/2007  Bates ................. G01N 15/1459
                                                                356/339

FOREIGN PATENT DOCUMENTS

| AU | WO 2011106850 A1 * | 9/2011 | ........... G01N 1/2205 |
|---|---|---|---|
| JP | 2944021 B2 | 8/1999 | |
| JP | 2005-514588 A | 5/2005 | |
| JP | 2010-281788 A | 12/2010 | |

OTHER PUBLICATIONS

Cheng, Y.S., et al., "Detection of Bioaerosols Using Multiwavelength UV Fluorescence Spectroscopy", Aerosol Science and Technology, Nov. 30, 2010, pp. 186-201.

* cited by examiner

*Primary Examiner* — Laura Martin
*Assistant Examiner* — Alex Devito
(74) *Attorney, Agent, or Firm* — Troutman Sanders LLP

(57) ABSTRACT

A particle detection system is provided, including a sensing chamber having an inlet nozzle, an outlet nozzle, and an interrogation zone defined therebetween. Particles in a sampled environmental gas are prevented from escaping the interrogation zone by pressurizing the sensing chamber such that the pressure therein is higher than that in the outlet nozzle. This is accomplished by providing a source of extra gas to the sensing chamber, for example, by diverting gas from an inlet flow path directly to the sensing chamber.

1 Claim, 7 Drawing Sheets

APPARATUS FOR DETECTING PARTICLES

CROSS REFERENCE TO RELATED APPLICATIONS

This application claims priority to U.S. Provisional Patent Application No. 61/614,395, filed on Mar. 22, 2012, which application is incorporated by reference herein in its entirety.

FIELD OF INVENTION

The present invention relates to apparatus and methods for detecting airborne particles and more particularly to apparatus and methods for containing particles to be measured within a laminar gas flow within a sensing chamber.

BACKGROUND OF INVENTION

A variety of manufacturing environments require strict control over the presence of foreign debris in the air. Semiconductor manufacturing, for example, has long required "clean-rooms" that use extensive air filtering to reduce the number and size of particles in the air to some acceptable level. Other manufacturing environments have similar but distinct requirements. For example, in pharmaceutical or medical device manufacturing environments, hospitals, and food processing or preparation environments, it is critical to control not only the number of particles in the air, but minimization of biologic particles is of particular importance. Microbial contamination, for example, can render an entire batch of pharmaceutical product unusable leading to significant monetary losses in the manufacturing process. Additionally, it is advantageous to have instantaneous detection of contamination events, including instantaneous information about whether a contamination event is biologic or non-biologic, during the manufacturing process for pharmaceuticals or medical devices.

Various systems and methods exist to detect and determine the size of airborne particles. Systems are also available to detect and characterize detected airborne particles as biologic or inert. For example, systems have been designed to detect the presence airborne particles by measuring the amount and directionality of light scattered by particles to determine particle size and the measurement of fluorescence excited in particles by illumination with a source light to classify measured particles as biological or non-biological.

In most conventional systems, fluid to be sampled (e.g., environmental air), is pulled into the system and introduced into a sensing chamber, for example, through an inlet nozzle. The fluid is then measured for particles in some way, for example, by illuminating the fluid with a beam of light. The fluid is then evacuated from the sensing chamber through an outlet nozzle.

This arrangement poses certain challenges. For example, particles may escape the flow of fluid between the inlet nozzle and the outlet nozzle and enter the sensing chamber. In other cases, particles may back up against the flow of fluid, and enter the sensing chamber though the outlet nozzle. In both cases, such particles can cross the illumination beam and scatter light or fluoresce, just as they would if they were being measured in the interrogation zone between the inlet and outlet nozzle. These particles create spurious optical emissions, which may be detected by the optical detectors in the particle detection system, thereby degrading the accuracy of the measurement data.

The problem is illustrated in FIGS. 1(a) and 1(b), which show a particle detection system 100. System 100 includes a sealed sensing chamber 102. Fluid (e.g., a gas) containing particles 115 is drawn into sensing chamber 102 and introduced thereto through inlet nozzle 105. The fluid is then drawn out of sensing chamber 102 through outlet nozzle 110 after temporarily occupying an interrogation zone 112. Negative pressure, is supplied by non-illustrated suction pump or blower in fluid communication with outlet nozzle 110. Ideally, suction pump provides a first negative pressure in the vicinity of 114, which is lower than a second negative pressure in the interrogation zone 112, which is lower still than the negative pressure at an exit aperture of inlet nozzle 105, which is lower still than the pressure in the ambient environment from with the fluid is drawn. Ideally, this ensures orderly flow of fluid from the environment, through the interrogation zone 112, and out through outlet nozzle 105.

While in interrogation zone 112, the fluid is illuminated by a light beam, generated by a light source, for example, a laser, laser diode or LED, in the vicinity of 135. While illuminated, particles in the fluid scatter light in the direction of 140, where scattered light may be detected by a scatter detector. Additionally, while illuminated, biological particles in the fluid fluoresce, and this fluorescence light is collected by an ellipsoidal reflector 125 and directed to a fluorescence detector in the vicinity of 130.

In certain systems, stray particles 142 can escape the fluid flow in the interrogation zone, leave the vicinity of the interrogation zone, and occupy other areas of the sensing chamber 102. Stray particles 142 are particles that either never reach outlet nozzle 110 to be evacuated from the system, particles that back up from outlet nozzle 110 (as shown in FIG. 1(b)), or particles from some other source. Such particles can create spurious readings at the fluorescence and scatter detectors, thereby degrading the accuracy of the measurement data. The presence of particles within the sensing chamber 102 outside of interrogation zone 112 is particularly troublesome as such particles can become deposited on the interior walls that define sensing chamber 112, from which they are difficult to dislodge.

A conventional solution for dealing with the problem of particles escaping the flow of fluid into a sensing chamber utilizes a "sheath flow" of clean air, which encapsulates the flow of particles under test as they travel through an interrogation zone. In a conventional arrangement an inlet nozzle is provided having an inner or central portion embedded in and surrounded by an outer annular portion. The outer annular portion divided into an upper and lower section. Environmental air from the upper annular section is diverted from an input stream. This "sheath air" is then filtered and accelerated with a sheath pump. The sheath air is then re-introduced into a lower annular section of the inlet nozzle. Meanwhile, air containing particles to be measured proceeds in the inner portion. In the region of the interrogation zone (i.e., near the input aperture to the sensing chamber), the lower annular section of both the central nozzle (carrying the air to be measured), and the outer annular portion taper to accelerate both flows of air. The combined air flows are then introduced to the interrogation zone, sampled, and then evacuated using a total flow pump. The result is that the air containing particles to be sampled is encapsulated in a relatively more quickly flowing sheath of clean, filtered air. This prevents particles from escaping the interior flow of sample air before both flows are drawn from the sensing chamber. A device operating according to this method is described in U.S. Pat. No. 5,561,515 to Hairston, et al., at FIG. 6.

SUMMARY OF THE INVENTION

Embodiments of the invention prevent particles from escaping a fluid flow under test by raising the pressure in the surrounding sensing chamber. This creates a uniform high-to-low pressure gradient from the interrogation zone into the outlet nozzle, which ensures that all particles are evacuated from the interrogation zone. The sensing chamber is pressurized in a number of ways. In one embodiment, filtered environmental air is drawn into the sensing chamber at a location remote from the interrogation zone using the negative pressure generated at the system's outlet nozzle. In other embodiments, a portion of the flow of air to be sampled is diverted prior to introduction to the inlet nozzle thereby creating a bypass flow. The bypass flow is then filtered, and its flow rate is regulated with an aperture. The bypass flow is then introduced to the sensing chamber at a position remote from the interrogation zone.

In another embodiment, a method and system for flushing a sensing chamber to dislodge and evacuate deposited particles in provided. In that embodiment, filtered environmental air, or bypass flow air, is introduced into a sensing chamber at more than one remote location. As this introduced air is drawn out of the sensing chamber, particles deposited on the interior of the sensing chamber are dislodged and removed.

In one embodiment, a particle detection system for detecting particles in an environmental gas is provided. The system includes a sensing chamber having an inlet flow nozzle fluidly coupled to the environmental gas, and an outlet flow nozzle. The inlet flow nozzle and the outlet flow nozzle define an interrogation zone. The system also includes an extra flow port located in the sensing chamber remote from the interrogation zone, the extra flow port being fluidly coupled between the sensing chamber and a source of extra gas.

In another embodiment, the system includes a source of negative pressure fluidly coupled to the outlet flow nozzle and capable of drawing environmental gas through the interrogation zone at a defined sample flow rate. In another embodiment, the extra flow port is fluidly coupled to the source of negative pressure through the exit nozzle such that the source of negative pressure is capable of drawing extra gas at a defined extra gas flow rate.

In certain embodiments, when the source of negative pressure is in operation, the ratio of the extra gas flow rate to the sum of the extra gas flow rate and the sample flow rate exceeds 0.21. In another embodiment, the source of negative pressure is in operation, the extra gas flow rate equals the sample flow rate. In another embodiment, when the source of negative pressure is in operation, a pressure in the sensing chamber exceeds a pressure at the outlet flow nozzle.

In certain embodiments, the extra flow port is fluidly coupled to a bypass flow path, which connects the inlet flow nozzle and the sensing chamber. In some embodiments, the bypass flow path comprises an adjustable orifice and a particle filter.

In another embodiment, the extra flow port of the system is fluidly coupled to a source of filtered environmental gas. In some embodiments, the system includes a second extra flow port located in the sensing chamber remote from the interrogation zone and the second extra flow port is fluidly coupled between the sensing chamber and an source of extra gas, and fluidly coupled to the first extra flow port.

Certain embodiments include a method of detecting particles in an environmental gas. The method involves drawing environmental gas to be sampled into a sensing chamber, measuring the environmental gas to be sampled to detect particles therein, evacuating environmental gas from the sensing chamber through an outlet nozzle, and pressurizing the sensing chamber such that its pressure is higher than that at the outlet nozzle.

In some embodiments, pressurizing the sensing chamber such that its pressure is higher than that at the outlet nozzle includes drawing extra gas into the sensing chamber. In other embodiments, measuring the environmental gas to be sampled to detect particles therein occurs in an interrogation zone, and drawing extra gas into the sensing chamber includes diverting a portion of the environmental gas to be sampled before it is introduced to interrogation zone and introducing the extra gas at a position in the sensing chamber remote from the interrogation zone.

In certain embodiments, drawing extra gas into the sensing chamber comprises supplying filtered environmental gas to the sensing chamber. In other embodiments, drawing extra gas into the sensing chamber comprises providing an extra gas flow path. In some embodiments, the extra gas flow path connects the sensing chamber to an inlet nozzle where environmental gas to be sampled is introduced to the sensing chamber. For some embodiments, the extra gas is filtered and flow-regulated prior to being introduced to the sensing chamber.

In some embodiments, environmental gas to be sampled is drawn into the sensing chamber at a first predefined rate and extra gas is drawn into the sensing chamber at a second predefined rate. In certain embodiments, the ratio of the first predefined rate and the sum of the first predefined rate and the second predefined rate exceeds 0.21.

Systems and methods according to the invention have certain advantages. For example, in contradistinction to the sheath flow method described above, systems and methods disclosed herein are entirely passive, relying only on the suction pump in fluid communication with the outlet nozzle to provide additional clean air flows to the sensing chamber. Thus, unlike in the sheath flow method, there is no need for an additional sheath flow pump. Additionally, systems using sheath flow generally use much higher total flow rates in the sheath air than in the sample air.

For example, Applicant understands that in one commercially available particle detection system that uses the sheath flow method, the Aerodynamic Particle Sizer® Model 3321, available from TSI Incorporated of St. Paul, Minn., the sample flow rate is 1 L/min and the sheath flow rate is 4 L/min, resulting in a total flow of 5 L/min. This results in a ratio of sheath flow to total flow of 0.8, meaning that 80% of the air being moved by the total flow pump is "wasted". This means that the total flow pump, tasked with evacuating all the air from the interrogation zone, must work much harder than it would otherwise have to work to simply draw into and evacuate from the interrogation zone the 1 L/min flow of air to be measured. The consequence of this is the need for larger pumps, generating greater amounts of waste heat, which is disadvantageous both from the standpoint of the physical package size of the particle detection system, and the ability of the system's sensitive optical and electronic systems to manage noise.

Systems in accordance with embodiments of the invention enable this additional pumping capacity to be used to pull more air to be sample, i.e., to achieve higher levels of throughput for air to be measured. Applicant has discovered that systems in accordance with the invention can eliminate the escaping particle problem by introducing an auxiliary or bypass flow to the sensing chamber that is smaller than the sample flow. This allows the majority of pumping power, which is a limitation in such systems, to be devoted to moving sample air.

Additionally, systems according to embodiments of the invention use a much simpler mechanical design, which does not rely on a complicated inlet nozzle geometry (i.e. inner nozzle embedded inside of outer nozzle).

DETAILED DESCRIPTION OF THE INVENTION

This invention is described in preferred embodiments in the following description with reference to the Figures, in which like numbers or indications represent the same or similar elements. References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The present invention is useful in a variety of detectors for detecting particles. Examples are particle size detectors and biologic particle detectors that detect both particle size and fluorescence to determine if a particle is a biologic or inert particle.

The present invention relates generally to methods for detecting airborne particles (generally, fluid-borne particles) in an air flow to be sampled, and more particularly to apparatus and methods that reduce particle deposition or escape from the sample air flow into the sensing chamber.

An example of a detection system with which the present invention can be used comprises one or more of the following elements:
a light source (for example, a laser, a laser diode or a LED);
optical components for the collection and focusing of scattered light and/or excited fluorescence on detectors;
one or more detectors for detecting scattered light (for example, a photodiode) and or one or more fluorescence detectors (for example, a PMT); and
one or more optical filters.
Detection systems may further comprise software, DAQ interface, and computer processor.

Other examples of detection systems that the current invention can be used with, include but are not limited to, those described in commonly owned U.S. patent application Ser. No. 12/642,705 Babico et al. and U.S. Pat. No. 7,430,046 to Jiang et al., the disclosures of which are incorporated herein by reference.

Figure 1:
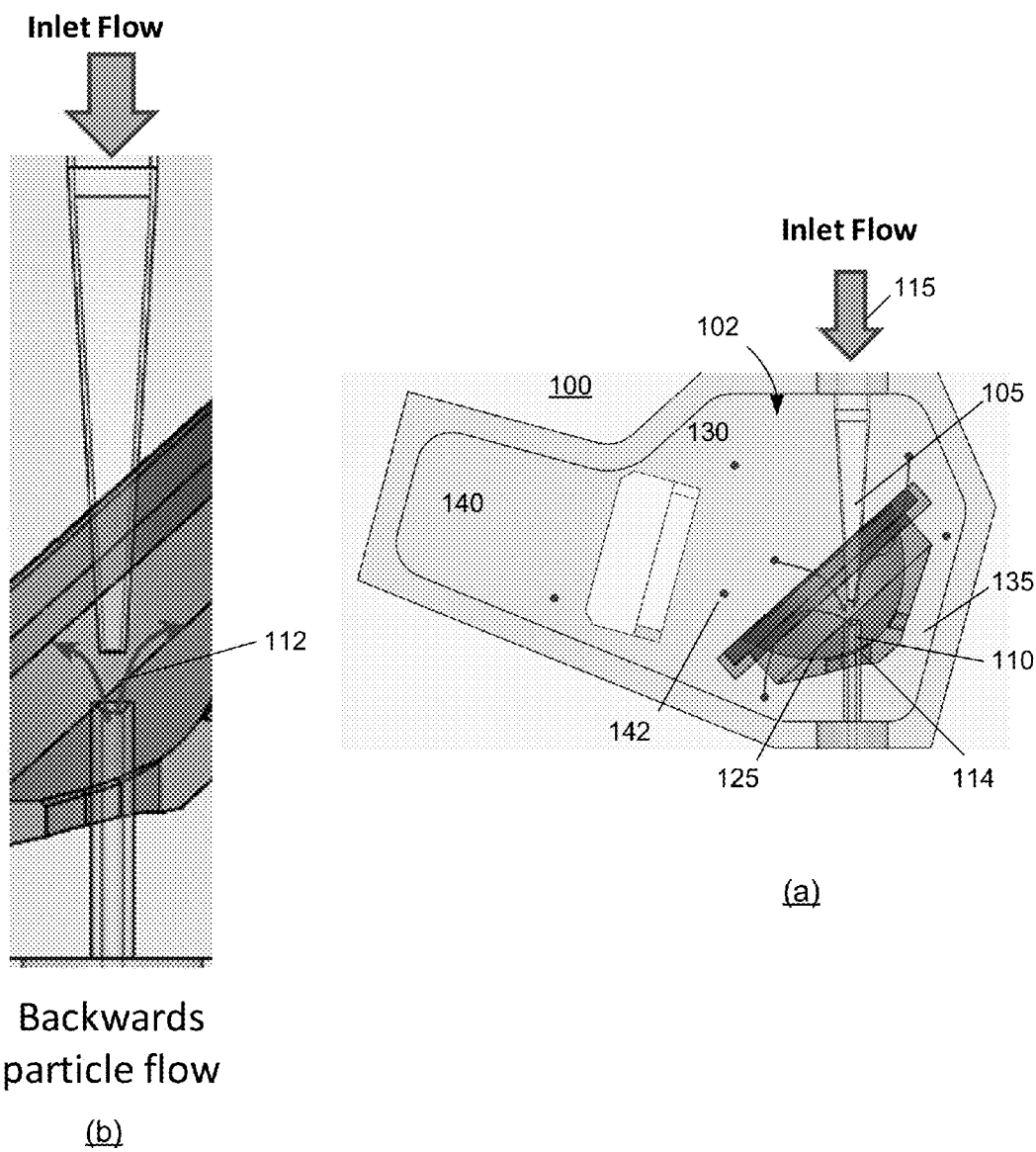
FIG. 1 is a schematic diagram showing the major mechanical features of a conventional particle detection system for the purposes of illustrating escaping particles.
Figure 2:
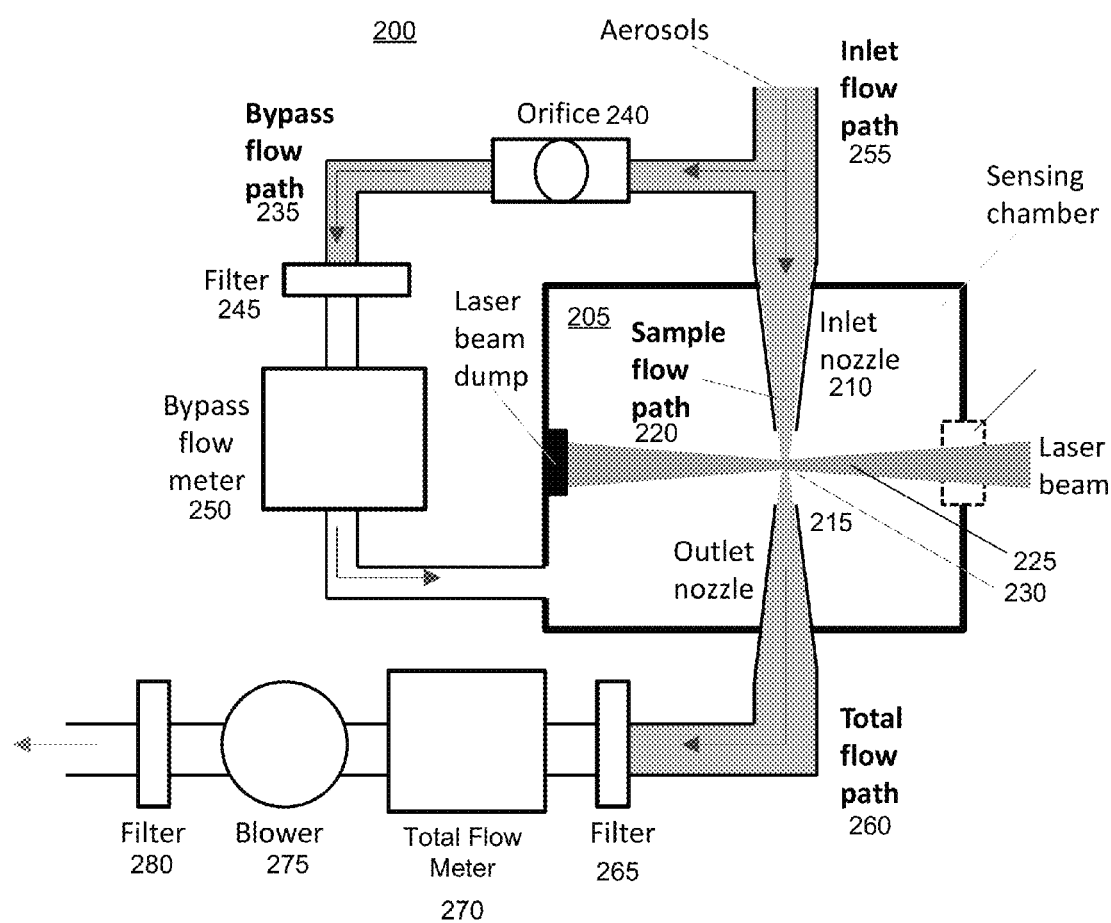
FIG. 2 is a schematic diagram of a particle detection system using bypass flow according to an embodiment of the invention.
Figure 3:
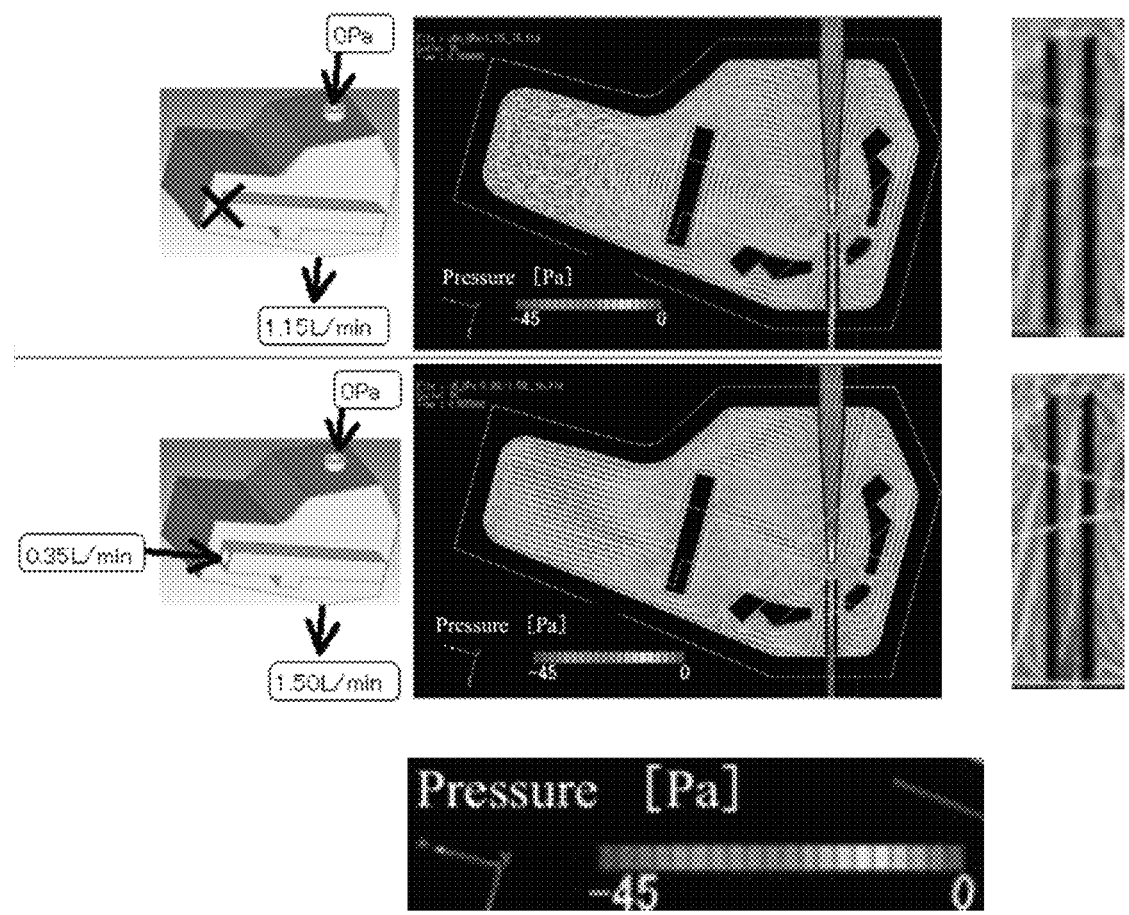
FIG. 3 shows the results of computational flow dynamics ("CFD") modeling for a particle detection system using bypass flow according to an embodiment of the invention.
Figure 4:
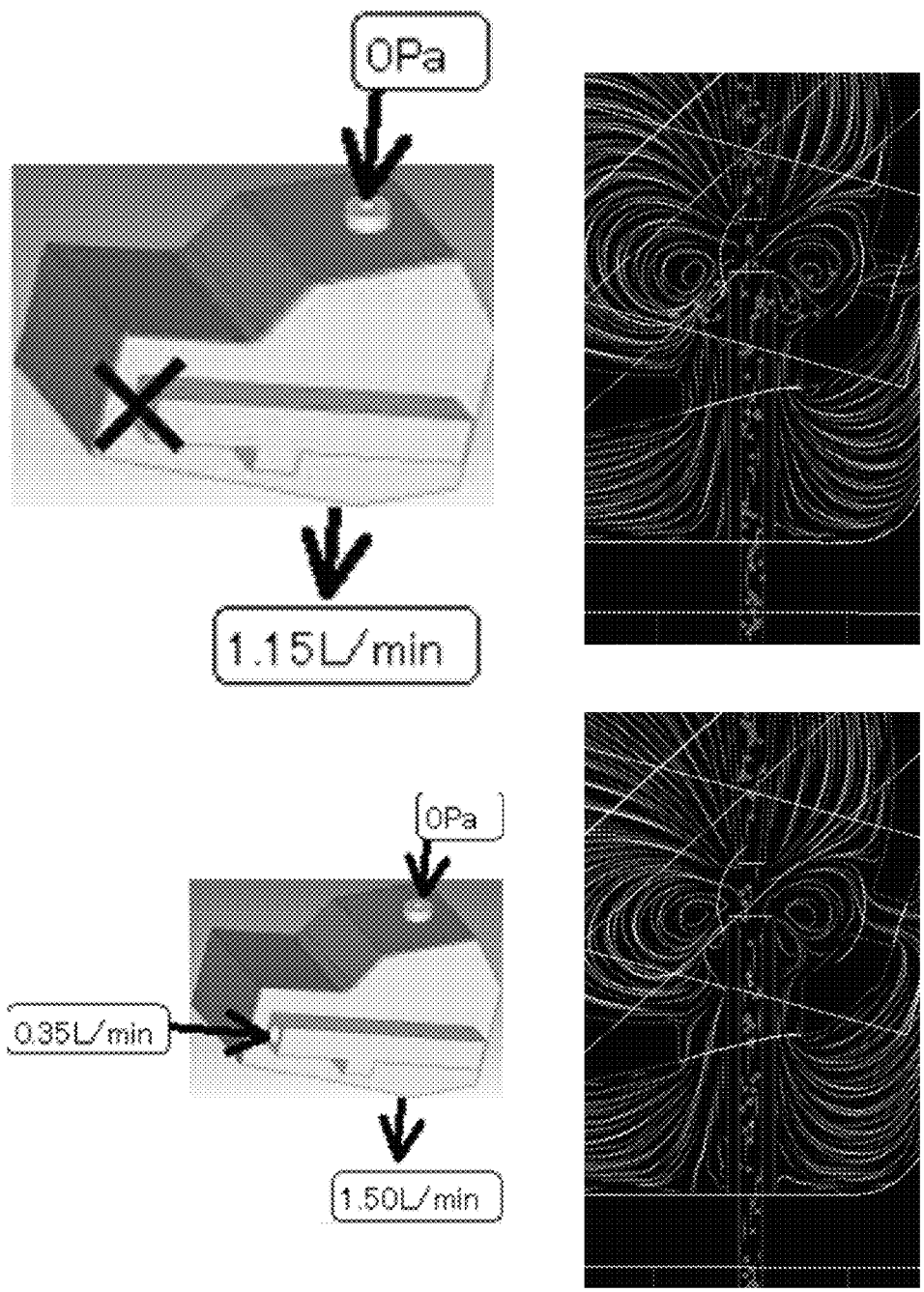
FIG. 4 shows the results of CFD modeling for a particle detection system using bypass flow according to an embodiment of the invention.

FIG. 2 is a schematic diagram of a particle detection system 200 using bypass flow according to an embodiment of the invention. The system of FIG. 2 comprises a sensing chamber 205. The sensing chamber 205 comprises an inlet nozzle 210 and an outlet nozzle 215. The inlet and outlet nozzles 210, 215 define a flow path 220 for air or other gas to flow through the sensing chamber so that particles that may be present in the air can be detected. A light beam 225 may be used to interrogate the air flow through a particle interrogation zone 230 located between the inlet and outlet nozzles in the sensing chamber for particles. The particle interrogation zone 230 is formed by a gap between the inlet and outlet nozzles 210, 215 across which particles in the air travel. The gap between the nozzles allows light from a light source to intercept the air flow.

In the sensing chamber, particles are detected when particles present in the laminar air (or gas) flow between the inlet and outlet nozzles 210, 215, pass through a light beam 225 (from a non-illustrated light source) in the particle interrogation zone 230 region and interact with the light beam 225. The light source may be a laser beam, a laser diode, an LED or other type of light source. The wavelength of the light beam 225 is chosen to interact with particles that may be present in the air flow and produce a signal that can be detected by one or more detectors. In preferred embodiments the light beam 225 is collimated or near collimated. For example, particles may interact with a laser beam to scatter light from which their particle size can be determined, or absorb one or more photons from the light and auto-fluoresce to determine if they are biologic in nature. In each instance one or more non-illustrated detectors are used to detect scattered light, fluorescence, or other signal caused by the interaction of the particles with the light beam.

To overcome the problem of particles escaping from the particle interrogation zone between the inlet and outlet air gap, the embodiment of FIG. 2 uses a secondary flow path, herein referred to as a "bypass flow path" 235, which introduces filtered air into the sensing chamber at a defined flow rate. The bypass flow path 235 comprises one or more of an adjustable orifice 240, a particle filter 245, a flow meter 250, tubing and one or more connectors. In the embodiment of FIG. 2, the adjustable orifice is set during calibration, but is not actively adjusted during operation. The bypass flow path 235 is coupled to sensing chamber 205 through a bypass flow or extra flow port in the interior wall of the sensing chamber. The bypass flow path 235 is connected to inlet flow path 255 to passively pressure balance the sensing chamber when the input pressure changes. The particle filter 245 in the bypass flow path removes particulates from the diverted inlet air flow so that air (or other gas) that is introduced into the sensing chamber is clean. By directly connecting the bypass flow path 235 with the inlet flow path, the pressure balance between the bypass and sample flow paths is maintained when the inlet pressure changes due to environmental conditions or factors. As a result pressure changes at the inlet flow path are evenly distributed along both bypass and sample paths, so no active pressure balancing system is required.

Bypass flow path 235 is connected to sensing chamber 205 at a location remote from interrogation zone 230. Thus, the interior of the sensing chamber, taken as a whole, receives a total flow rate equal to that present in the inlet flow path 255 and the bypass flow path 235. Accordingly, total flow path 260, which is connected to outlet nozzle 215, carries air (or other gas) at a rate equal to the sum of the inlet flow path and bypass flow path rates. The system of FIG. 2 includes a filter 265, a total flow meter 270, a blower or suction pump 275 and another filter 280, which filters measured air before it is exhausted from the system. Blower 275 supplies negative pressure to outlet nozzle 215 sufficient to draw measured air across interrogation zone 230 at a predetermined rate, given the geometry components of the inlet flow path 255, the inlet nozzle 210, and the geometry and components of the bypass flow path 235, in particular, the diameter of orifice 240.

The flow rate across interrogation zone 230 is typically a boundary condition for optimizing the components of the system of FIG. 2. In Applicant's system, a flow rate through the interrogation zone of 1.15 L/min is desired. This flow rate is determined by pulse width of the optical signal. Applicant's optical detectors and associated electronics are designed and calibrated to detect, as well as the geometry of the laser beam, in the vicinity of the interrogation zone 230. Applicant experimentally determined that with a 1.15 L/min sample flow rate, a minimum bypass flow rate of 0.35 L/min was beneficial for preventing escaping particles. Thus, in the system of FIG. 2, the pull-rate of blower 275 and the diameter of orifice 240 are selected to yield 1.15 L/min flow at the interrogation zone, while also pulling the minimum volume of bypass flow air to prevent particle escape. In accordance with Applicant's experimental results, in one embodiment, the bypass flow is 0.35 L/min, yielding a total flow rate of 1.50 LPM.

Experimental and analytical results indicate that this effect is scalable, and that other flow rates may also be used. In particular, Applicant has discovered that the effectiveness of preventing escape of particles from the interrogation zone or outlet nozzle depends on the ratio of the bypass flow rate to the total flow rate. In particular, a ratio of bypass flow rate to total flow rate greater than 0.21 has been found to be effective in preventing escaping particles. In one embodiment the bypass flow ratio used is 0.23.

Figure 5:
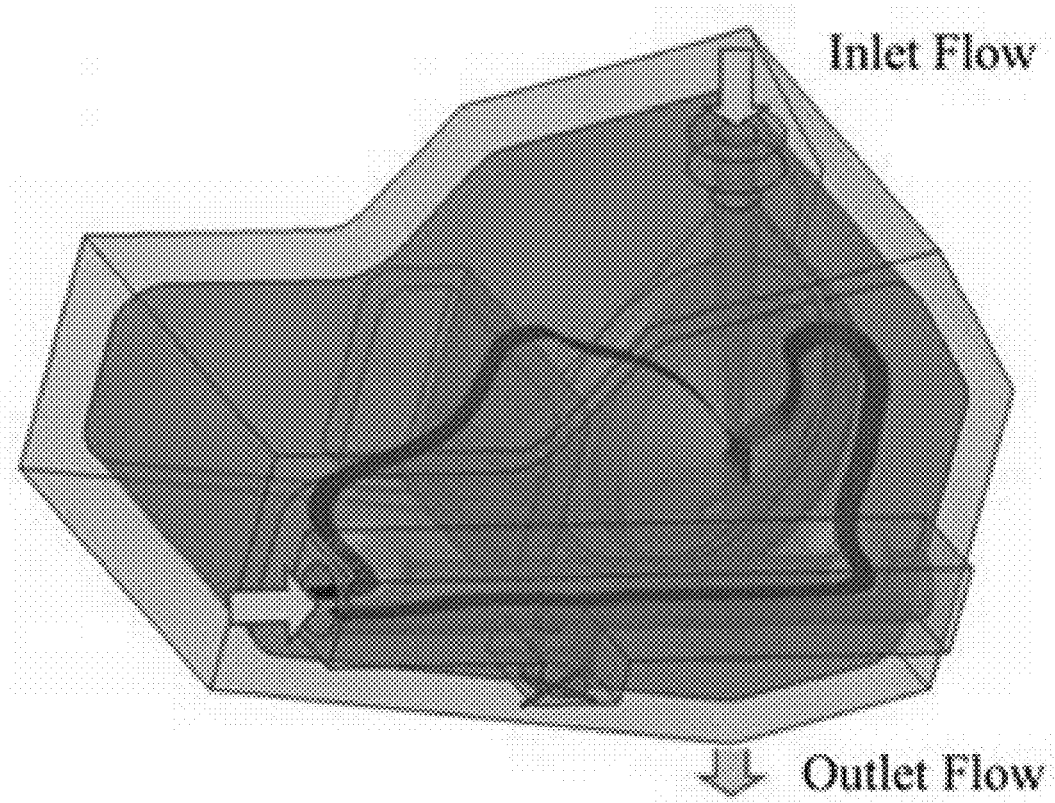
FIG. 5 is a schematic diagram showing a system for purging a sensing chamber according to an embodiment of the invention.

The escape of particles from the particle interrogation zone between the inlet and outlet nozzles is controlled by pressure balance. The pressure in the sensing chamber is raised by making a hole (port) in the sensing chamber and introducing bypass flow though the hole. The pressure increase in the sensing chamber provides a pressure balance between the internal sensing chamber volume and the outlet nozzle, thereby significantly reducing or preventing the back-flow of particles, or the escape of particles from the particle interrogation zone.

Modeling of the invention by Computational Fluid Dynamics ("CFD") illustrates the advantages of the bypass flow of the present invention. This is illustrated in FIG. 3, which shows the results of CFD modeling for a particle detection system using bypass flow according to an embodiment of the invention. The embodiment shown in FIG. 3 is a system having the geometry of the system depicted in FIG. 1, but improved with the bypass flow method of the instant invention. In accordance with embodiments of the invention, bypass air flow may be introduced into the sensing chamber through a port placed at a suitable location in walls of the sensing chamber. Exact placement will depend on other elements present in the chamber such as optical lenses, mirrors, detectors, etc, for detecting particles. In the embodiment of FIG. 3, the bypass flow port is placed in the vicinity of reference numeral 140 of FIG. 1. In the embodiment of FIG. 3, bypass, or equivalently, extra flow, is provided such that the entirety of the sensing chamber is pressurized to have a lower pressure than the pressure at the inlet nozzle, but a higher pressure than the pressure at all locations within the outlet nozzle below the sampling region. In other words, the adjustable orifice of a bypass (or extra gas) flow path and the overall flow rate (determined by a source of negative coupled to the outlet nozzle) are selected such that the pressure in the entirety of the chamber exceeds the pressure at all locations within the outlet nozzle below the sampling region. As is seen in FIG. 3, CFD modeling of the geometry of the sensing chamber of FIG. 1, with the bypass flow port placed in a remote location from the interrogation zone, and the sample, bypass and total flow rates set forth above with respect to the embodiment of FIG. 2, yielded extremely good CFD results. In particular, without bypass flow, pressure in outlet nozzle is similar to sensing chamber causing particle backflow. With bypass flow, pressure in outlet nozzle is significantly lower than sensing chamber thereby preventing particle backflow.

FIG. 4 illustrates the particle transfer efficiency between the nozzles with and without bypass flow using CFD simulations. Particle sizes of 0.1 um, 0.3 um, 0.5 um and 5.0 um were simulated. It is expected that small size particles will be more sensitive to escaping due to lower mass and inertia compared with larger particle sizes. As can be seen in FIG. 4, without bypass flow particles escape the air flow path between the nozzles. Introduction of bypass flow substantially reduces or eliminates particles escaping the air flow. Again, for the modeling of FIG. 4, the experimentally determined bypass flow rate of 0.35 L/min, with the optimum sample flow rate of 1.15 L/min, and the geometry of the system of FIG. 1 were used.

Thus far, the phrase "bypass flow" has been used to describe the flow of additional air, apart from sample air, which is introduced to the sensing chamber of a particle detection system in order to pressure balance the sensing chamber and prevent backflow and escape of particles from the interrogation zone. Indeed, the embodiment of FIG. 2 shows a bypass flow path, where extra air is diverted from the sampled air, along a bypass path, and is filtered and introduced to the sensing chamber. Those skilled in the art will appreciate, however, that any source of extra flow which raises the pressure of the sensing chamber relative to the pressure of the outlet nozzle will accomplish much of the advantageous effect observed by Applicant in the system of FIG. 2. For example, in certain embodiments of the invention, the pressure of the sensing chamber is raised by providing an "extra flow" path from some source of air (or other gas) to the sensing chamber comprising a port connected to the sensing chamber, an "extra flow" flow meter, a filter, an adjustable orifice, and associated tubing and connecting fittings. In other words, in certain embodiments, the "bypass flow path" depicted schematically in FIG. 2 connects, not to the inlet flow path, but to the environmental air, bottled gas, or any other suitable source of gas. The bypass configuration of FIG. 2 is preferred, however, as connecting the bypass flow path to the input flow path makes the system insensitive to pressure changes upstream of the inlet flow path, i.e., in the environment being sampled.

Applicant has determined, both experimentally and through CFD modeling, that systems according to embodiments of the invention are remarkably insensitive to the location of the bypass flow port, i.e., the precise location where the bypass or extra flow is introduced to the sensing chamber. In certain embodiments, the inlet port to the sensing chamber for the bypass flow may be connected to a manifold that provides for two or more air inlets inside of the sensing chamber, or for the bypass air to be introduced at specific locations in the sensing chamber. For example, in one embodiment the bypass flow can be introduced in the region of the particle in interrogation zone. In additional embodiments, bypass air flow is introduced to the sensing chamber at two different points along two different paths, which may originate from a single bypass port. An example of the latter arrangement is shown in FIG. 5. The manifold inside of the sensing chamber can be made of any suitable material compatible with the system.

Figure 6:
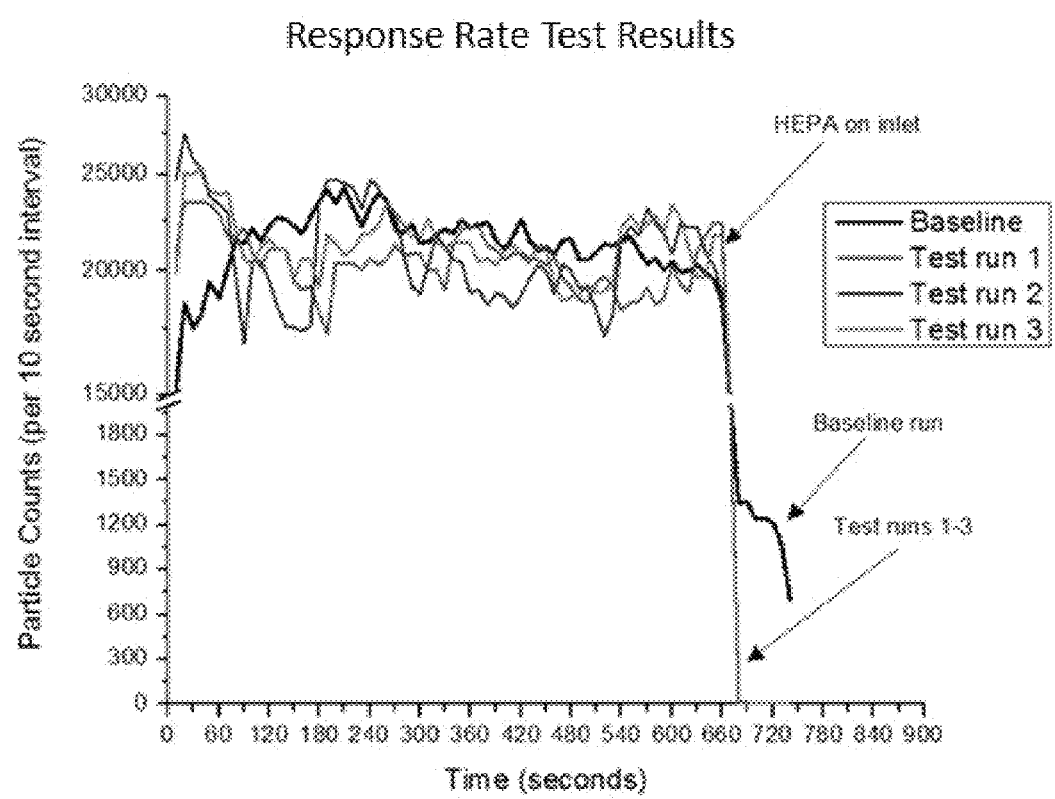
FIG. 6 shows test results for a sensing chamber purge conducted according to a method according to an embodiment of the invention.

The embodiment of FIG. 5 has additional utility as a means of flushing or purging the sensing chamber in the event of contamination. Contamination may occur in a number of ways, for example, if the sensing chamber is opened for service, if particles escape the sample flow and are deposited within the chamber, etc. Using the geometry of the particle detection system shown in FIG. 5, including the two-port manifold shown, applicant conducted experiments according to ISO 21504-1 to determine the rate at which the manifold geometry of FIG. 5, operating at a bypass or extra flow rate of 0.35 L/min, would flush the interior of the sensing chamber. In accordance with the ISO test standard, the sensing chamber was intentionally contaminated by flowing 0.5 micros polystyrene beads into the chamber for ten minutes at a flow rate of 1.15 L/min at a concentration sufficient to measure 2000 counts per second in the sensing chamber. A bypass flow rate into the manifold of 0.35 L/min was also maintained. The contamination flow was then cut off with a HEPA filter for 10 seconds, effectively eliminating the incoming contamination particles in the sample flow, and particle count measurements were taken to determine the remaining particles left in the system. The results of this test are shown in FIG. 6. As can be seen, with a bypass flow of 0.35 L/min, the particle count was drastically reduced. The experimental data showed particle count rates after the 10 second flush period of only 0.03% of the peak contamination particle count rate. Thus, systems according to embodiments of the invention including bypass flow, at the rates specified above, are essentially self-cleaning, and will reliably flush particles that may enter the sensing chamber outside of the interrogation zone from whatever source.

Figure 7:
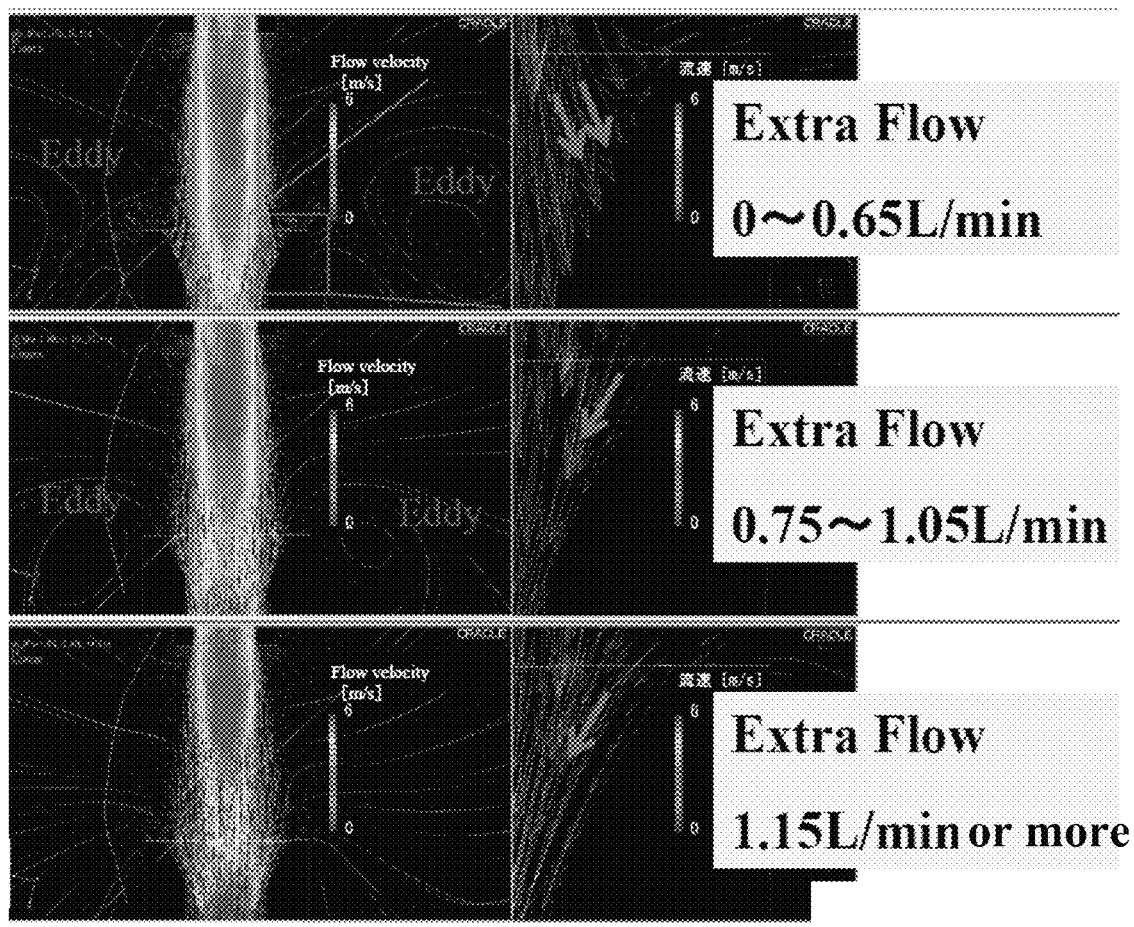
FIG. 7 shows the results of CFD modeling for a particle detection system using bypass flow according to an embodiment of the invention to eliminate eddies in the vicinity of the outlet nozzle.

Additional CFD modeling of systems according to embodiments of the invention is shown in FIG. 7. Applicant has determined that using the geometry and the sample flow rate of 1.15 L/min set forth above that eddies of turbulence in the vicinity of the outlet nozzle may be eliminated using slightly higher bypass flow rates. In particular, turbulence in the vicinity of the outlet nozzle is completely eliminated at a bypass flow rate of 1.15 L/M, i.e., is equal to the sample flow rate. This condition would further minimize the risk of particles escaping the sample flow into the sensing chamber.

While the preferred embodiments of the present invention have been illustrated in detail, it should be apparent that modifications and adaptations to those embodiments may occur to one skilled in the art without departing from the scope of the present invention as set forth in the following claims.

What is claimed is:

1. A method of detecting particles in an environmental gas, comprising:

drawing environmental gas to be sampled into a sensing chamber;

measuring the environmental gas to be sampled to detect particles therein;

evacuating environmental gas from the sensing chamber through an outlet nozzle, and pressurizing the sensing chamber such that its pressure is higher than that at the outlet nozzle, wherein measuring the environmental gas to be sampled to detect particles therein occurs in an interrogation zone, and wherein drawing extra gas into the sensing chamber comprises diverting a portion of the environmental gas to be sampled before it is introduced to interrogation zone and introducing the extra gas at a position in the sensing chamber remote from the interrogation zone.

* * * * *